United States Patent
Lewerenz et al.

(10) Patent No.: US 9,421,268 B2
(45) Date of Patent: Aug. 23, 2016

(54) PEDIATRIC ORAL LIQUID COMPOSITIONS CONTAINING NEPADUTANT

(71) Applicant: LABORATORI GUIDOTTI S.P.A., Pisa (IT)

(72) Inventors: Claudia Lewerenz, Berlin (DE); Reinhard Schmitz, Berlin (DE); Maria Altamura, Florence (IT)

(73) Assignee: LABORATORI GUIDOTTI S.P.A., Pisa (IT)

( * ) Notice: Subject to any disclaimer, the term of this patent is extended or adjusted under 35 U.S.C. 154(b) by 0 days.

(21) Appl. No.: 14/414,449

(22) PCT Filed: Jul. 12, 2013

(86) PCT No.: PCT/IB2013/055754
§ 371 (c)(1),
(2) Date: Jan. 12, 2015

(87) PCT Pub. No.: WO2014/009926
PCT Pub. Date: Jan. 16, 2014

(65) Prior Publication Data
US 2015/0165034 A1    Jun. 18, 2015

(30) Foreign Application Priority Data

Jul. 12, 2012  (IT) ............................ RM2012A0331

(51) Int. Cl.
| | | |
|---|---|---|
| A61K 31/451 | (2006.01) | |
| A61K 31/55 | (2006.01) | |
| A61K 38/12 | (2006.01) | |
| A61K 47/22 | (2006.01) | |
| A61K 47/18 | (2006.01) | |
| A61K 9/00 | (2006.01) | |
| A61K 47/26 | (2006.01) | |
| A61K 47/38 | (2006.01) | |
| A61K 38/14 | (2006.01) | |
| A61K 47/12 | (2006.01) | |

(52) U.S. Cl.
CPC ............... *A61K 47/22* (2013.01); *A61K 9/0053* (2013.01); *A61K 9/0095* (2013.01); *A61K 38/12* (2013.01); *A61K 38/14* (2013.01); *A61K 47/12* (2013.01); *A61K 47/183* (2013.01); *A61K 47/26* (2013.01); *A61K 47/38* (2013.01)

(58) Field of Classification Search
None
See application file for complete search history.

(56) References Cited

U.S. PATENT DOCUMENTS

2008/0090795 A1 *  4/2008  Aleotti ................... A61K 31/00
                                                              514/210.2
2010/0234284 A1    9/2010  Aleotti et al.

FOREIGN PATENT DOCUMENTS

| EP | 1 712 220 | 10/2006 | |
|---|---|---|---|
| WO | 2006/045820 | 5/2006 | |
| WO | WO 2006108556 A2 * | 10/2006 | ........... A61K 9/0043 |

OTHER PUBLICATIONS

Altamura, "Tachykinin NK2 receptor antagonists. A patent review (2006-2010)," Exp. Opin. Therap. Patents 22:57-77 (published online Dec. 2011).*
Akers, "Sterile Drug Products: Formulation, Packaging, Manufacturing, and Quality," Informa Healthcare, 22 pp., Chapt. 8 (2010).*
Int'l Search Report for PCT/IB2013/055754, three pages (Nov. 2013).
Written Opinion for PCT/IB2013/055754, seven pages (Nov. 2013).
Eastman "Eastman Vitamin E TPGS NF applications and properties passage 20051001" No. PCI-102B, pp. 1-24 (Oct. 2005).

* cited by examiner

*Primary Examiner* — Julie Ha
*Assistant Examiner* — Kristina M Hellman
(74) *Attorney, Agent, or Firm* — Nixon & Vanderhye PC

(57) ABSTRACT

Oral liquid pharmaceutical compositions containing as active ingredient Nepadutant, PGS as solubilizer and optionally a chelating agent. Such compositions are found to be very stable and suitable for paediatric use in the treatment of gastro-intestinal diseases.

19 Claims, No Drawings

PEDIATRIC ORAL LIQUID COMPOSITIONS CONTAINING NEPADUTANT

This application is the U.S. national phase of International Application No. PCT/IB2013/055754 filed 12 Jul. 2013, which designated the U.S. and claims priority to Italian Patent Application No. RM2012A000331, filed 12 Jul. 2012; the entire contents of each of which are hereby incorporated by reference.

SUMMARY

Oral liquid pharmaceutical compositions containing as active ingredient Nepadutant, PGS as solubilizer and optionally a chelating agent. Such compositions are found to be very stable and suitable for paediatric use in the treatment of gastro-intestinal diseases.

FIELD OF THE INVENTION

The present invention relates to novel pharmaceutical compositions containing an antagonist of tachykinin NK2 receptor, i.e. Nepadutant, very slightly soluble in aqueous solutions.

These pharmaceutical compositions are stable solutions, designed for oral administration of the active ingredient and preferably intended for use in neonates and infants for paediatric gastrointestinal diseases. The high stability of the compositions is due to the use of TPGS as a solubilizer additive optionally with the addition of a chelating agent.

BACKGROUND

Contrary to what happens in most preparations of animal tissues where it is necessary to block both NK1 and NK2 receptors to obtain a more efficient antagonism against the spasmogenic effect induced by tachykinins, in other preparations, including preparations of isolated human intestine, the antagonists of NK2 receptor are already fully effective against the spasmogenic effect induced by exogenous or endogenous tachykinins.

In addition to the stimulation role in the regulation of intestinal motility, the activation of tachykinin NK2 receptors, also triggers both intrinsic and extrinsic inhibitory mechanisms to the intestinal wall (Giuliani et al. J. Pharmacol. Exp Ther. 246:322-327 (1988)). Moreover NK2 tachykinin receptors regulate intestinal permeability (Hallgren et al. Am. J. Physiol. 273: G1077-G1086 (1997)) and are also involved in the regulation of the secretion of water and ions in the gut epithelium in rats and in humans (Tough et al. Naunyn-Schmiedeberg's Arch Pharmacol. 367:104-108 (2003), and in the modulation of visceral sensitivity (Julia et al. Gastroenterology 107:94-102 (1994)), especially when altered by an active or previous inflammatory state or by a stressful situation.

These pharmaceutical aspects of tachykinins have suggested the assessment of selective antagonists of the tachykinin NK2 receptor in the development of drugs directed against gastrointestinal diseases characterized by gut motility disorders and visceral hypersensitivity such as, for example, irritable bowel syndrome in adults (Lecci et al. Curr. Opin. Invest. Drugs 3:589-601 (2002)).

Nepadutant is a selective antagonist of the tachykinin NK2 receptor with formula (I), originally described in EP815126. It is bicyclic hexapeptide, with an excellent safety profile and tolerability.

The NK2 antagonist, Nepadutant, can be identified as [N$^4$-(2-acetylamino-2-deoxy-β-D-glucopyranosyl)-L-asparaginyl-L-α-triptophan-L-phenylalanyl-L-2,3-diaminopropionil-L-leucil]-C-4.2-N-3.5-lattame-C-1.6-N-2.1-lattame or cyclic[3-amino-L-alanil-L-leucil-N-[2-(acetylamino)-2-deoxy-β-D-glucopyranosyl]-L-asparaginyl-L-α-aspartyl-L-triptophan-L-phenylalanyl](4→1)-lattame (9Cl) (CAS RN: 183747-35-5)) (alternatively known as MEN11420).

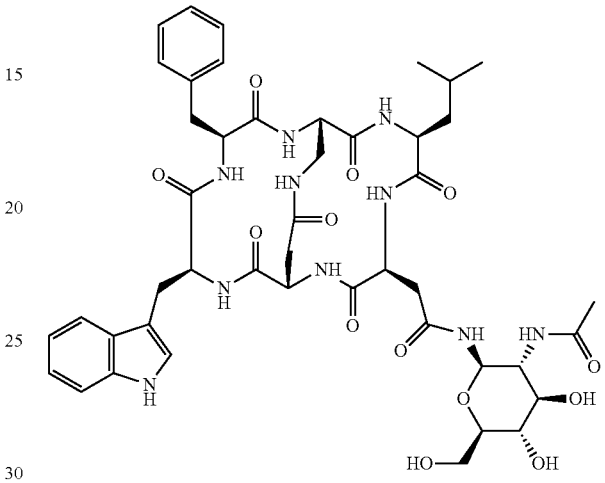

(I)

Nepadutant has shown good activity in various in vitro and in vivo models and in humans in reversing the side effects of the activation of NK2 receptors in the intestine, such as visceral hyperalgesia or alterations of the intestinal motility.

It has been recently discovered that Nepadutant is absorbed when administered orally in new born animals (rats or mice), contrary to what is found in adult animals. Furthermore, the oral administration of Nepadutant in new born rats is able to block, up to 24 hours after its administration, the increase in intestinal transit induced by the activation of NK2 receptors, without altering the basal parameters. In addition Nepadutant has proven effective in a model of hyperalgesia in new born rats.

These results suggest the oral potential bioavailability even in newborns and therefore the clinical use of Nepadutant in the symptomatic treatment of gastrointestinal disorders (e.g. infantile colic), as claimed in WO2006045820.

The EMA recommends the use of oral solutions for newborns and infants (nurslings) (from 28 days to 23 months) as the preferred dosage form (EMEA/CHMP/PEG/194810/2005). On the other hand the parenteral formulations (e.g. intravenous) are strongly contraindicated especially for not life-threatening diseases. Thus, it was essential to develop an oral solution of Nepadutant for paediatric use in the gastrointestinal disorders.

Nepadutant is poorly soluble in aqueous medium and has a bitter taste. Furthermore, it is stable in the dried state but the solutions of Nepadutant are sensitive to oxidative degradation.

In WO2006045820 pharmaceutical compositions containing paediatric Nepadutant in liquid form are described (pages 7-8, Examples 1-4), and such compositions are characterized by the use of polysorbate as solubilizer; such compositions appear to be not completely satisfactory for their storage limited duration at room temperature or at a high temperature.

EP1464341 describes an ophthalmic solution/emulsion comprising TPGS (Vitamin E TPGS 1000 also referred to as d-alpha tocopheryl polyethylen glycol 1000 succinate) and the antioxidant active ingredient ubiquinone. Combinations of ubiquinone, TPGS and magnesium ascorbyl-2-phosphate show synergistic antioxidant effects. It is not described, however, any antioxidant effect on any active ingredient which is an antagonist of the tachykinin NK2 receptor in solutions containing TPGS.

In WO97/35587 the formation of liquid formulations containing an HIV protease inhibitor, TPGS and a hydrophilic non-aqueous solvent miscible with TPGS is disclosed, preferred for the filling of soft gelatine capsules. The formulations show a higher bioavailability of the HIV protease inhibitor. The non-aqueous solvent is essential for this formulation.

WO99/26607 describes a distribution system based on a liquid crystal structure, in which the drug is dissolved directly in TPGS. In order to maintain the drug in solution the solid structure of cyclosporine with TPGS does not require the presence or absence of emulsifiers, co-solvents, surfactants, or other solubilizer agents. The resulting products, such as controlled release capsules, tablets, pills are solid oral dosage forms. Because TPGS is used as the sole solvent, high amounts of TPGS (50% to 99.9%) are required.

U.S. Pat. No. 5,583,105 describes pre-concentrated emulsion containing the active ingredient cyclosporine in a lipophilic and/or amphiphilic solvent. In this composition TPGS is mentioned as an emulsifier, adjuvant and antioxidant for fat oils. The antioxidant effect on a pharmaceutical active ingredient, and especially on a NK2 receptor antagonist, is not claimed.

WO2006036614 describes materials like surfactants suitable for solid formulations. The TPGS row material of waxy consistency is converted into properly shaped solid that can be incorporated for example into tablets. The use of the solid form for the preparation of solutions and/or emulsions is not described.

EP1216025 describes the use of a wide range of TPGS as a surfactant (from 0.1% to 90%) in solid formulations comprising a dispersant soluble in water and a soluble compound in lipid medium as a lipase inhibitor. The solidified mixture is loaded into HPMC capsules that reveal an increase in the efficiency and power.

Formulations for topical use containing TPGS and layers of alpha-tocopherol to solubilize or emulsify water insoluble drugs are mentioned in WO9531217.

TPGS is described as a stabilizer applied for the formation and stabilization of double-layer liposomes in acid environment (U.S. Pat. No. 5,364,631).

In WO9808490 the preparation of solid co-precipitated for oral delivery of lipophilic substances with poor biodisponibility is described. Delivery tests are conducted on dry powders.

DESCRIPTION OF THE INVENTION

The present invention relates to stable oral, liquid, pharmaceutical compositions containing Nepadutant and TPGS, even for paediatric use for the treatment of newborns and infants (nurslings) in the period from birth to one year, and preferably, from birth to six months of age.

The TPGS is a substance with solubilizer and antioxidant activity therefore acts as a stabilizer of substances which are highly unstable to oxidation. In addition, the TPSG is essentially tasteless and therefore suitable and acceptable for use in neonates and nurslings. Surprisingly the use of TPGS results in a solubilizing and antioxidant action allowing to obtain limpid, stable solutions of Nepadutant and acceptable from an organoleptic point of view. Additional excipients commonly used with TPGS, such as lipophilic or hydrophilic non-aqueous solvents or co-solvents, lipophilic antioxidant phases etc. are therefore not necessary to generate a stable liquid formulation.

Therefore objects of the present application are liquid aqueous oral pharmaceutical compositions comprising as active ingredient Nepadutant and TPGS as an additive.

In a specific embodiment of the invention, the compositions contain the TPGS as the only solubilizer and/or stabilizing additive.

In another embodiment of the invention the compositions may further comprise a chelating agent. In a further embodiment of the invention the compositions comprise in addition to the TPGS other pharmaceutically acceptable excipients.

A second object of the invention is the compositions containing Nepadutant, TPGS and optionally a chelating agent and other optional excipients for use in a paediatric treatment in neonates or nurslings, in particular for the paediatric treatment of gastrointestinal diseases.

A further object of the present application is a process for the preparation of the composition of the invention.

Formulations designed for paediatric use should be in liquid dosage forms for oral administration.

The purified water is a solvent appropriate for paediatric formulations. However, due to the poor water solubility of Nepadutant, in order to dissolve a pharmaceutical effective amount, the use of at least one solubilizer, surfactant or emulsifier is essential.

Few solubilizers, surfactants or emulsifiers are suitable for paediatric formulations, since most of the solubilizers/surfactants or emulsifiers produce side effects.

Solubilizers which are very used are polymers of Poloxamer type, for example, the Poloxamer 188 ® (Poloxamer 188 termone indicates a copolymer between the polyoxypropilen and polyoxyethylene and polyoxypropilene of an approximately molecular mass of 1800 g/mol with a content of 80% w/w of polyoxyethylene). However, it has not been possible to obtain the necessary solubilisation of Nepadutant in water with Poloxamer 188 (Table1).

TABLE 1

Solubility in water of Nepadutant with different concentrations of solubilizer at 25° C.

| % of Poloxamer 188 in water | soluble nepadutant [mg/mL] |
|---|---|
| — | 0.13 |
| 0.50% | 0.20 |
| 1.00% | 0.21 |
| 2.00% | 0.28 |
| 2.50% | 0.31 |

Polysorbates are widely used such as solubilizers, in oral, topical formulations and even in parenteral ones. The polysorbates are also accepted as a food additive in Europe (E433). Typical examples of compositions of Nepadutant with polysorbate 80 are those described in WO2006045820 (e.g. 1-4 on page 7-8). A disadvantage of polysorbates is the bitter taste of the excipient. The use of flavourings and/or sweeteners to mask the bitter taste of active ingredients and/or excipients is the approach mostly used in paediatric oral formulations, with raspberry and cream aromas frequently identified as possible excipients masking the flavour, that generate the preferred taste sensation. However, the formulations containing polysorbates Nepadutant proved poorly stable at room temperature.

In order to increase the stability of solutions containing Nepadutant, the packaging of the formulation and procedures for filling multiple doses containers must be conducted under conditions of deaeration in the presence of inert gases such as nitrogen and argon. These conditions represent an additional problem in the industrial process of packaging, an increasing of total costs and are insufficient to completely prevent the instability of formulations containing polysorbates.

A potential alternative to the conditions of deaeration may be the use of an antioxidant. Thus, various compositions containing different antioxidants have been studied.

It has been assayed the effect of different standard antioxidants and their mixtures on the stability of the paediatric formulation in oral solution of Nepadutant 0.4 mg/mL containing polysorbate 80 as a solubilizer (Table 2).

TABLE 2

| Ingredient | A | B | C | D | E | F | G | H | I | J | K |
|---|---|---|---|---|---|---|---|---|---|---|---|
| Nepadutant | 0.4 | 0.4 | 0.4 | 0.4 | 0.4 | 0.4 | 0.4 | 0.4 | 0.4 | 0.4 | 0.4 |
| Polysorbate 80 | 12.5 | 12.5 | 12.5 | 12.5 | 12.5 | 12.5 | 12.5 | 12.5 | 12.5 | 12.5 | 12.5 |
| Dextrose | 400.0 | 400.0 | 400.0 | 400.0 | 400.0 | 400.0 | 400.0 | 400.0 | 400.0 | 400.0 | 400.0 |
| Sorbic acid | 1.0 | 1.0 | 1.0 | 1.0 | 1.0 | 1.0 | 1.0 | 1.0 | 1.0 | 1.0 | 1.0 |
| Sodium carboxymethylcellulose | 20.0 | 20.0 | 20.0 | 20.0 | 20.0 | 20.0 | 20.0 | 20.0 | 20.0 | 20.0 | 20.0 |
| Raspberry flavour | 0.035 | 0.035 | 0.035 | 0.035 | 0.035 | 0.035 | 0.035 | 0.035 | 0.035 | 0.035 | 0.035 |
| Cream flavour | 0.015 | 0.015 | 0.015 | 0.015 | 0.015 | 0.015 | 0.015 | 0.015 | 0.015 | 0.015 | 0.015 |
| Citric acid | 20 | — | — | 20 | 20 | — | — | 20 | — | — | — |
| Propyl gallate | — | 0.1 | — | 0.1 | — | 0.1 | — | — | 0.1 | — | — |
| Edetate sodium | — | — | 0.1 | — | 0.1 | 0.1 | — | — | — | 0.1 | — |
| Bis-sodium Bisulphite | — | — | — | — | — | — | 10 | 10 | 10 | 10 | — |
| Purified water | ad 1.0 ml | ad 1.0 ml | ad 1.0 ml | ad 1.0 ml | ad 1.0 ml | ad 1.0 ml | ad 1.0 ml | ad 1.0 ml | ad 1.0 ml | ad 1.0 ml | ad 1.0 ml |

TABLE 3

The Nepadutant content in paediatric formulations in oral solution containing different amounts of antioxidants and their mixtures after storage at 40° C./75% RH (in percentage of the initial Nepadutant content).

| | Antioxidant | | | | | | |
|---|---|---|---|---|---|---|---|
| Months | A | B | C | D | E | F | K |
| 0 | 100.0 | 100.0 | 100.0 | 100.0 | 100.0 | 100.0 | 100.0 |
| 1 | 68.5 | 97.5 | 89.0 | 92.5 | 80.7 | 101.5 | 82.9 |
| 2 | 51.1 | 95.2 | 79.0 | 82.7 | 65.1 | 99.8 | 70.3 |

After storage for 2 months at accelerated conditions (40° C./75% RH) the content of Nepadutant was determined (Table 3, 4). Surprisingly, the formulations containing citric acid showed a significant decrease in Nepadutant content compared to a reference formulation without the addition of antioxidant (Table 3). These results could be caused by a significant decrease in the formulation pH from pH 5 to ca. pH 3.

No effect on the increased stability on the Nepadutant content has been found for the formulations containing edetate sodium. However, formulations containing propyl gallate, the so-called "super antioxidant", and a mixture of propyl gallate and edetate sodium showed a significant increase in the stability of Nepadutant.

However, the propyl gallate is not allowed in foods for infants and young children, because of the known tendency to cause the blood disorder methemoglobinemia.

Incompatibilities have been found with sodium bisulfide and sodium bisulfide mixtures containing antioxidants. The initial concentration of the formulations of Nepadutant was found to be ca. 20% of the declared Nepadutant content (Table 4).

TABLE 4

The Nepadutant content in paediatric formulations in oral solution containing different amounts of antioxidants and their mixtures after storage at 40° C./75% RH (in percentage of the initial Nepadutant content).

| | Antioxidant | | | | |
|---|---|---|---|---|---|
| Months | G | H | I | J | K |
| 0 | 21.5 | 21.7 | 17.6 | 19.6 | 100.0 |
| 1 | n, t, | n, t, | n, t, | n, t, | 84.2 |
| 2 | n, t, | n, t, | n, t, | n, t, | 79.2 |

The use of TPGS according to the present invention offers solution to all the problems related to the compositions of the prior art, specifically connected to the difficult solubilisation of Nepadutant, to its instability to oxidation and the need to achieve the organoleptic characteristics of the composition also acceptable from the paediatric population.

The purpose of comparing the effect of water-soluble antioxidant additives based on Vitamin E selected from the group: TPGS (Vitamin E TPGS 1000 or d-alpha tocopheryl polyethylen glycol 1000 succinate), L-ascorbic acid dl-alpha-tocopherol phosphate potassium salt and dispersible pre-formulated such as dried mixtures of tocopherols at 30% (vitamin E finely dispersed in a matrix of modified food starch) and vitamin E dried at 15% CC (alpha tocopherol acetate finely dispersed in a matrix of modified food starch), were added to a typical pharmaceutical composition containing polysorbate (example 2) to study the increase in the stability of dissolved Nepadutant (table 5). During packaging and the subsequent filling process no deaeration with inert gases such as nitrogen or argon has been used.

TABLE 5

Nepadutant recovery after storage of solutions at 40° C./75% RH

| Formulations | Antioxidant | Time [months] | [%] recovered nepadutant |
|---|---|---|---|
| Example 1 (formulation K) | none | 0 | 100.0 |
|  |  | 1 | 82.9 |
|  |  | 2 | 70.3 |
| Example 2 | TPGS 3 mg/ml | 0 | 100.0 |
|  |  | 1 | 94.4 |
|  |  | 2 | 89.5 |
| Example 2 | Dry mixed tocopherols 30% 1.8 mg/ml | 0 | 100.0 |
|  |  | 1 | 93.2 |
|  |  | 2 | 87.8 |
| Example 2 | L-ascorbic acid dl-alfa-tocoferol phosphate potassium salt 2.3 mg/ml | 0 | 100.0 |
|  |  | 1 | 83.5 |
|  |  | 2 | 77.3 |
| Example 2 | Dry vitamin E 15% 3.9 mg/ml | 0 | 100.0 |
|  |  | 1 | 83.5 |
|  |  | 2 | 77.1 |

An interesting increase in stability has been achieved with TPGS. Surprisingly, the composition with TPGS as antioxidant proves to be very stable, making unnecessary the addition of antioxidants as well as the procedure of deaeration with inert gases.

Moreover, equally surprisingly it was found that TPGS can also function as a powerful and efficient solubilizer for Nepadutant to get the preferred concentrations in aqueous solutions (Table 6).

TABLE 6

Solubility of Nepadutant in aqueous solutions of TPGS at 25° C.

| Solubilizer concentration [%] | Nepadutant concentration [mg/ml] |
|---|---|
| 0.5 | 1.60 |
| 1.0 | 3.39 |
| 2.0 | 3.59 |
| 2.5 | 3.59 |

Consequently TPGS can be used as solubilizer instead of polysorbate 80 giving rise to a composition in solution form with a substantially better taste even when formulated without flavouring (Example 3).

The formulation containing TPGS shows a better acceptance from the organoleptic point of view.

Table 7) organoleptic rank for different Nepadutant formulations

The compositions were tasted, in double-blind, by six researchers who have expressed a qualitative judgment on three possibilities:

*Bad: slightly unpleasant taste, or bitter or presence of unpleasant aftertaste

**Indifferent: no appreciable taste

***Good: pleasant taste

| Formulation | Flavour | Organoleptic rank |
|---|---|---|
| based on Polysorbate | no | * |
| based on Polysorbate | yes | ** |
| based on TPGS | yes | *** |
| based on TPGS | no | *** |

* Bad,
** Indifferent,
*** Good

The stability of the formulations (Table 8) can be further increased if a chelating agent is added (Example 4).

TABLE 8

Recovery of Nepadutant after maintenance of solutions at 40° C./75% RH

| Formulation | Solubilizer | Chelating agent | Time [months] | [%] recovered nepadutant |
|---|---|---|---|---|
| Example 3 | TPGS | none | 0 | 100.0 |
|  |  |  | 1 | 95.7 |
|  |  |  | 2 | 91.4 |
| Example 4 | TPGS | sodium diedetate | 0 | 100.0 |
|  |  |  | 1 | 99.2 |
|  |  |  | 2 | 96.5 |

A preferred composition, in the form of aqueous solution, according to the present invention, comprises:
a) from 0.01% to 1% w/v (i.e. from 0.1 mg/ml to 10 mg/ml) of nepadutant
b) from 0.1% to 20% w/v (i.e. from 1 mg/ml to 200 mg/ml) of TPGS
c) optionally from 0.001% to 0.1% w/v (i.e. from 0.01 mg/ml to 1 mg/ml) of a chelating agent
d) one or more pharmaceutically acceptable excipients.

According to the present invention, the liquid oral pharmaceutical composition comprises the active ingredient Nepadutant in an amount from 0.01% to 1% w/v and preferably from 0.025% to 0.5% w/v.

The composition comprises as solubilizer and/or stabilizing the TPGS in an amount of at least 0.1% w/v, preferably from 0.1% to 20% w/v, for example from 0.5% to 5% w/v.

In the composition the weight ratio between Nepadutant and the solubilizer TPGS is in the range from 1:1 to 1:50, preferably in the range from 1:2 to 1:40 for example in the range from 1:4 to 1:30.

The composition according to the present invention can possibly comprise a chelating agent selected from the group of ethylenediaminetetraacetic acid (EDTA), disodium (ethylendinitrile) tetraacetate dihydrate (disodium edetate), and disodium-[(ethylenedinitryl) tetraacetate] hydrocalcium (calcium sodium diedetate). The chelating agent may be present in the composition in an amount of from 0.001% to 0.1% w/v, preferably from 0.005% to 0.05%, or from 0.005% to 0.02% w/v.

Other pharmaceutically acceptable excipients for paediatric use may be present, such as sweeteners (such as sugars, including dextrose), additional solubilizer agents (such as polyvinylpyrrolidone, sodium carboxymethylcellulose) and preservatives (e.g. Sorbic acid and ascorbic acid).

Examples of compositions according to the invention include:
a) Nepadutant 0:40 mg/ml, TPGS 10:00 mg/ml, dextrose 400.00 mg/ml, sorbic acid 1:00 mg/ml, sodium carboxymethylcellulose 20:00 mg/ml, purified water qs 1.0 ml.
b) Nepadutant 0:40 mg/ml, TPGS 10:00 mg/ml, diedetate sodium 0.100 mg/ml, dextrose 400.00 mg/ml, sorbic acid 1:00 mg/ml, sodium carboxymethylcellulose 20:00 mg/ml, purified water qs 1.0 ml.

c) Nepadutant 2:00 mg/ml, TPGS 10:00 mg/ml, diedetate sodium 0.100 mg/ml, dextrose 400.00 mg/ml, sorbic acid 1:00 mg/ml, sodium carboxymethylcellulose
20.0 mg/ml, purified water qs 1.0 ml.

In order to administer these compositions to the patient, they may be added to foods used for the nutrition of infants, particularly to milk, in beverages or liquid foods.

The composition may be administered in a single or multiple daily dose, depending on doctor's advice, for the treatment of gastrointestinal disease in neonates and infants aged from birth to one year, and preferably, from birth to six months.

The present invention further relates to a process for the preparation of pharmaceutical compositions such as those described above, which process comprises mixing Nepadutant with TPGS, and optionally a chelating agent, with one or more pharmaceutically acceptable excipients.

Some examples of aqueous solutions packaged in accordance with the formulation described are shown below.

EXAMPLES

Formulations containing polysorbate 80 as solubilizer.

Example 1 (Comparative Example)

The formulation is quite similar to that described in WO2006045820 and was prepared in an inert atmosphere.

A dry premix consisting of dextrose, sorbic acid, sodium carboxymethylcellulose, and flavourings was prepared. Such a premix is dissolved in purified water (ca. 60% of the total amount) to a temperature of 35° C.-40° C. while stirring and homogenizing in a special machine for mixing.

Subsequently, the solution is cooled to a temperature of 20° C.-25° C. and polysorbate 80, Nepadutant and the remaining amount of water (40% of the total quantity) is added by shaking and homogenising in an inert gas atmosphere. The formulation is stirred until obtaining a limpid and homogeneous solution.

| Ingredient | Amount [mg/ml] |
|---|---|
| Nepadutant | 0.40 |
| Polysorbate 80 | 12.50 |
| Dextrose | 400.00 |
| Sorbic Acid | 1.00 |
| sodium carboxymethylcellulose | 20.00 |
| Raspberry flavour | 0.035 |
| Cream flavour | 0.015 |
| Purified Water | qs 1.0 ml |
| Inert Gas | q.s. |

This formulation also corresponds to the formulation K in the Table 2, 3 and 4.

Example 2 (Comparative Example)

Compositions similar to those of Example 1 with in addition an antioxidant are prepared in accordance with Example 1, containing in addition an antioxidant. The presence of antioxidant makes the deaeration with inert gas not required.

by A dry premix consisting of dextrose, sorbic acid, sodium carboxymethylcellulose, and flavourings is prepared. Such a premix is dissolved in purified water (ca. 60% of the total amount) to a temperature of 35° C.-40° C. while stirring and homogenizing in a special machine for mixing.

Subsequently, the solution is cooled to a temperature of 20° C.-25° C. and to it is added polysorbate 80, the antioxidant, Nepadutant and the remaining amount of water (40% of the total quantity) by stirring and homogenizing. The formulation is stirred until obtaining a limpid and homogeneous solution.

The antioxidant used is selected from the group: TPGS (vitamin E polyethylene glycol 1000 succinate or Vitamin E TPGS NF grade) 3 mg/ml, L-ascorbic acid dl-alpha-tocopherol phosphate potassium salt 2.3 mg/ml, vitamin E dried to 15% CC (alpha tocopherol acetate finely dispersed in a matrix of modified food starch) 3.9 mg/ml, mixtures of tocopherols dried to 30% (vitamin E finely dispersed in a matrix of modified food starch) 1.8 mg/ml.

Formulations Containing TPGS as Solubilizer

Example 3

This example illustrates a liquid formulation comprising aqueous Nepadutant TPGS as solubilizer. This formulation was packaged without deaeration with inert gas.

by A dry premix consisting of dextrose, sorbic acid and sodium carboxymethylcellulose is prepared. Such a premix is dissolved in purified water (ca. 60% of the total amount) to a temperature of 35° C.-40° C. while stirring and homogenizing in a special machine for mixing, in an inert gas atmosphere.

Subsequently, the solution is cooled to a temperature of 20° C.-25° C. and to it is added 20% w/v solution of TPGS, Nepadutant and the remaining amount of water (40% of the total quantity) by stirring and homogenizing. The formulation is stirred until obtaining a limpid and homogeneous solution.

| Ingredient | Amount [mg/ml] |
|---|---|
| Nepadutant | 0.40 |
| TPGS | 10.00 |
| Dextrose | 400.00 |
| Sorbic Acid | 1.00 |
| carboxymethylcellulose sodium | 20.00 |
| Purified Water | qs 1.0 ml |

Example 4

This example illustrates a liquid formulation comprising aqueous Nepadutant TPGS as solubilizer. This formulation was packaged without deaeration with inert gas and comprises in addition edetate disodium as a chelating agent.

A dry premix consisting of dextrose, sorbic acid and sodium carboxymethylcellulose is prepared. Such a premix is dissolved in purified water (ca. 60% of the total amount) to a temperature of 35° C.-40° C. while stirring and homogenizing in a special machine for mixing.

Subsequently, the solution is cooled to a temperature of 20° C.-25° C. and to it is added 20% w/v solution of TPGS, edetate sodium, Nepadutant and the remaining amount of water (40% of the total amount) by stirring and homogenizing in an inert gas atmosphere.

The formulation is stirred until obtaining a limpid and homogeneous solution.

| Ingredient | Amount [mg/ml] |
|---|---|
| Nepadutant | 0.40 |
| TPGS | 10.00 |
| Sodium diedetate | 0.10 |
| Dextrose | 400.00 |

-continued

| Ingredient | Amount [mg/ml] |
|---|---|
| Sorbic Acid | 1.00 |
| sodium carboxymethylcellulose | 20.00 |
| Purified Water | qs 1.0 ml |

Example 5

At the same manner as in Example 4, the following composition can be prepared

| Ingredient | Amount [mg/ml] |
|---|---|
| Nepadutant | 2.00 |
| TPGS | 10.00 |
| Sodium diedetate | 0.10 |
| Dextrose | 400.00 |
| Sorbic Acid | 1.00 |
| sodium carboxymethylcellulose | 20.00 |
| Purified Water | qs 1.0 ml |

The invention claimed is:

1. A liquid aqueous oral pharmaceutical composition comprising nepadutant as active ingredient, d-alpha-tocopheryl polyethylene glycol succinate (TPGS), and a chelating agent, and optionally other pharmaceutical acceptable excipients.

2. The pharmaceutical composition according to claim 1, wherein nepadutant is present in an amount from 0.01% to 1% weight/volume of the total composition.

3. The aqueous pharmaceutical composition according to claim 2, wherein nepadutant is present in an amount from 0.025% to 0.5% weight/volume on the total composition.

4. The aqueous pharmaceutical composition according to claim 1, wherein TPGS is present in an amount of at least 0.1% weight/volume of the total composition.

5. The aqueous pharmaceutical composition according to claim 4, wherein TPGS is present in an amount from 0.1% to 20% weight/volume on the total composition.

6. The aqueous pharmaceutical composition according to claim 5, wherein TPGS is present in an amount from 0.5% to 5% weight/volume of the total composition.

7. The aqueous pharmaceutical composition according to claim 1, wherein the ratio between nepadutant and TPGS is from 1:1 to 1:50.

8. The aqueous pharmaceutical composition according to claim 1, wherein the ratio between nepadutant and TPGS is from 1:2 to 1:40.

9. The aqueous pharmaceutical composition according to claim 1, wherein the ratio between nepadutant and TPGS is from 1:4 to 1:30.

10. The aqueous pharmaceutical composition according to claim 1, wherein the chelating agent is selected from the group consisting of EDTA, edetate disodium, and edetate calcium disodium.

11. The aqueous pharmaceutical composition according to claim 10, wherein the chelating agent is present in an amount comprised from 0.001% to 0.1% w/v of the total composition.

12. The aqueous pharmaceutical composition according to claim 11, wherein the chelating agent is present in an amount comprised from 0.005% to 0.05% w/v of the total composition.

13. The aqueous pharmaceutical composition according to claim 11, wherein the chelating agent is present in an amount comprised from 0.005% to 0.02% w/v of the total composition.

14. The aqueous pharmaceutical composition according to claim 1, further comprising pharmaceutical acceptable excipients selecting from the group consisting of sweeteners, preservatives, and solubilizers.

15. The liquid aqueous oral pharmaceutical composition according to claim 1, comprising
    a) from 0.01% to 1% w/v of nepadutant,
    b) from 0.1% to 20% w/v of TPGS,
    c) from 0.001% to 0.1% w/v of chelating agent, and
    d) one or more pharmaceutically acceptable excipients.

16. The aqueous oral pharmaceutical composition according to claim 14, selected from the group consisting of
    a) nepadutant 0.40 mg/ml, TPGS 10.00 mg/ml, dextrose 400.00 mg/ml, sorbic acid 1.00 mg/ml, sodium carboxymethyl cellulose 20.00 mg/ml, and purified water qs 1.0 ml;
    b) nepadutant 0.40 mg/ml, TPGS 10.00 mg/ml, edetate disodium 0.100 mg/ml, dextrose 400.00 mg/ml, sorbic acid 1.00 mg/ml, sodium carboxymethyl cellulose 20:00 mg/ml, and purified water qs 1.0 ml; and
    c) nepadutant 2.00 mg/ml, TPGS 10.00 mg/ml, edetate disodium 0.100 mg/ml, dextrose 400.00 mg/ml, sorbic acid 1.00 mg/ml, sodium carboxymethyl cellulose 20.00 mg/ml, and purified water qs 1.0 ml.

17. A method of treating a newborn or nursling of colic, the method comprising orally administering an aqueous oral pharmaceutical composition according to claim 1 to the newborn or nursling in need thereof.

18. A method of treating a pediatric gastrointestinal disease, the method comprising orally administering an aqueous oral pharmaceutical composition according to claim 1 to the pediatric patient in need thereof, wherein the gastrointestinal disease is characterized by a gut motility disorder.

19. A process for the preparation of the composition according to claim 1, comprising mixing nepadutant, TPGS, and a chelating agent.

* * * * *